US007262300B2

(12) United States Patent
Cooper

(10) Patent No.: US 7,262,300 B2
(45) Date of Patent: Aug. 28, 2007

(54) POLYMORPHIC FORMS OF A GABA$_A$ AGONIST

(75) Inventor: Vincent Brett Cooper, Cheshunt (GB)

(73) Assignee: Merck Sharp & Dohme Ltd., Hoddesdon, Hertfordshire (GB)

( * ) Notice: Subject to any disclaimer, the term of this patent is extended or adjusted under 35 U.S.C. 154(b) by 335 days.

(21) Appl. No.: 11/045,768

(22) Filed: Jan. 28, 2005

(65) Prior Publication Data
US 2005/0171142 A1 Aug. 4, 2005

(30) Foreign Application Priority Data
Jan. 30, 2004 (GB) ................... 0402118.4

(51) Int. Cl.
*C07D 471/02* (2006.01)
*C07D 491/02* (2006.01)
(52) U.S. Cl. ..................... 546/115; 546/116
(58) Field of Classification Search ............. 546/115, 546/116
See application file for complete search history.

(56) References Cited
U.S. PATENT DOCUMENTS

| 4,278,676 A | 7/1981 | Krogsgaard-Larsen |
| 4,301,287 A | 11/1981 | Krogsgaard-Larsen |
| 4,315,934 A | 2/1982 | Christensen |
| 4,362,731 A | 12/1982 | Hill |
| 5,929,065 A | 7/1999 | Lancel |

FOREIGN PATENT DOCUMENTS

| EP | 0000338 | 6/1978 |
| WO | WO 02/40009 | 5/2002 |
| WO | WO 02/094225 | 11/2002 |
| WO | WO 2004/112786 | 12/2004 |
| WO | WO 2005/023256 | 3/2005 |
| WO | WO 2005/023820 | 3/2005 |
| WO | WO 2005/073237 | 8/2005 |
| WO | WO 2006/013397 | 2/2006 |
| WO | WO 2006/053556 | 5/2006 |
| WO | WO 2006/083682 | 8/2006 |
| WO | WO 2006/102093 | 9/2006 |
| WO | WO 2006/118897 | 11/2006 |

OTHER PUBLICATIONS

Lipkowitz et al. Journal of Molecular Structure, 195 (1989) 65-77.*
Soren Munk Madsen, "Quantitative Determination of the Gamma-Aminobutyric Acid Agonist, 4,5,6,7-Tetrahydroisoxazolo[5,4-c]pyridine-3-OL, in Serum by High-Performance Liquid Chromatography", *Journal of Chromatography*, p. 209-218, 274, (1983).
Soren Munk Madsen, "Pharmacokinetics of the Gamma-Aminobutyric Acid Agonist THIP (Gaboxadol) Following Intramuscular Administration to Man, with Oberservations in Dog", *Acta Pharmacol. et toxicol*, p. 353-357, 53, (1983).
Richard Huckle, "Gaboxadol Lundbeck/Merck", *Current Opinion in Investigational Drugs*, p. 766-773, 5(7), 2004.

* cited by examiner

*Primary Examiner*—D. Margaret Seaman
*Assistant Examiner*—Nizal S. Chandrakumar
(74) *Attorney, Agent, or Firm*—J. Eric Thies; William Krovatin

(57) ABSTRACT

Two new crystalline monhydrates and two new crystalline anhydrates of gaboxadol are disclosed together with methods for preparing them.

5 Claims, No Drawings

POLYMORPHIC FORMS OF A GABA$_A$ AGONIST

CROSS REFERENCE TO RELATED APPLICATIONS

This application claims priority under 35 U.S.C. § 119 from GB Application No. 0402118.4, filed Jan. 30, 2004.

This invention is concerned with novel polymorphic forms of the compound 4,5,6,7-tetrahydroisoxazolo[5,4-c]pyridin-3-ol in both anhydrous and hydrated states. The invention is further concerned with pharmaceutical compositions containing said polymorphic forms as an active ingredient, with the use of said polymorphic forms in medicine, and with methods for the preparation of said polymorphic forms.

The compound 4,5,6,7-tetrahydroisoxazolo[5,4-c]pyridin-3-ol (also known as THIP or gaboxadol, and hereinafter referred to as gaboxadol) and is a known GABA$_A$ receptor agonist (see, for example, EP 0 000 338) and has therefore been suggested for use in treating a variety of neurological and psychiatric disorders such as epilepsy, Parkinson's disease, schizophrenia and Huntingdon's chorea. More recently, there has been disclosed the use of gaboxadol for treatment of sleep disorders (WO 97/02813) and premenstrual syndrome (WO 02/40009), and the disclosure that gaboxadol is a particularly potent agonist at GABA$_A$ receptors comprising α4 and δ subunits (Brown et al, *British J. Pharmacol.*, 136, 965-74 (2002).

Other indications for which gaboxadol may be suitable include hearing disorders (especially tinnitus), vestibular disorders, attention deficit hyperactivity disorder, intention tremor and restless leg syndrome.

The preparation of gaboxadol is disclosed in EP 0 000 338, both as the free base and as an acid addition salt (specifically, the hydrobromide), but here is no mention of hydrated forms, and the hydrobromide was the form used for the pharmacological testing described in EP 0 000 338.

Gaboxadol is sold commercially (eg. by Sigma) in the form of the hydrochloride salt, and WO 01/22941 and WO 02/094225 disclose granulated pharmaceutical compositions comprising gaboxadol in the form of the hydrochloride salt.

As detailed in WO 02/094255, use of acid addition salts of gaboxadol such as hydrochloride in the manufacture of pharmaceutical oral dosage forms such as tablets gives rise to corrosion problems when conventional techniques and equipment are employed. There is therefore a need for novel forms of gaboxadol suitable for incorporation in pharmaceutical oral dosage formulations.

According to the invention, in a first aspect thereof, there is provided the compound gaboxadol monohydrate in a crystalline form. In particular, said crystalline form is selected from:

(a) form I which is characterised by an X-ray powder diffraction spectrum in 2θ values using CuKα radiation having a peak at 11.5°; and (b) form II which is characterised by an X-ray powder diffraction spectrum in 2θ values using CuKα radiation having a peak at 25.2°.

According to a second aspect of the invention, there is provided the compound gaboxadol anhydrate in a crystalline form selected from:

(a) form I which is characterised by an X-ray powder diffraction spectrum in 2θ values using CuKα radiation having a peak at 12.8°; and (b) form II which is characterised by an X-ray powder diffraction spectrum in 2θ values using CuKα radiation having a peak at one or more of 16.0°, 24.7° and 28.4°.

According to a third aspect of the invention there is provided a method of preparing crystalline gaboxadol monohydrate of form I as defined above comprising the steps of:

(a) dissolving an acid addition salt of gaboxadol in water;
(b) adding sufficient base to provide a pH of about 6.5; and
(c) collecting the resulting precipitate immediately.

According to a fourth aspect of the invention there is provided a method of preparing crystalline gaboxadol monohydrate of form II as defined above comprising the steps of:

(a) dissolving an acid addition salt of gaboxadol in water;
(b) adding sufficient base to provide a pH of about 6.5;
(c) aging the resulting mixture for at least 12 hours; and
(d) collecting the resulting solid.

According to a fifth aspect of the invention there is provided a method of preparing crystalline gaboxadol anhydrate of form I as defined above by heating crystalline gaboxadol monohydrate of form I at a temperature above 100° C. at atmospheric pressure.

According to a sixth aspect of the invention there is provided a method of preparing crystalline gaboxadol anhydrate of form II as defined above by heating crystalline gaboxadol monohydrate of form II at a temperature above 100° C. at atmospheric pressure.

According to a seventh aspect of the invention there is provided a method of preparing crystalline gaboxadol anhydrate of form II as defined above by stirring a suspension of gaboxadol anhydrate of form I as defined above in ethanol at ambient temperature.

For the avoidance of any doubt, "gaboxadol" as used herein refers to 4,5,6,7-tetrahydroisoxazolo[5,4-c]pyridin-3-ol free base, which is believed to exist as the zwitterion:

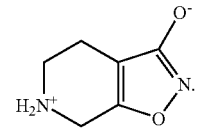

When an acid addition salt of gaboxadol such as the hydrochloride or hydrobromide (preferably the hydrochloride) is dissolved in water and neutralised with a suitable base (e.g. sodium hydroxide, potassium hydroxide or a water-soluble tertiary amine, preferably triethylamine), gaboxadol monohydrate precipitates in a crystalline form herein designated as form I. The same product is obtained if the neutralisation is carried out in an aqueous-organic mixture using sodium hydroxide as base, preferably at about 0° C. The organic component of the mixture is typically an alcohol (e.g. n-propanol or 2,2,2-trifluoroethanol) or a water-miscible solvent such as acetone, tetrahydrofuran, dimethoxyethane, N-methylpyrrolidone or N,N-dimethylacetamide. The water content of the mixture is typically in the range 30%-70%, preferably 40%-50%. The pH after neutralisation is typically 6.5±0.5, preferably 6.5. This crystalline form is characterised by the X-ray powder diffraction spectrum having a peak at 11.5° (2θ). Other peaks that may additionally be present include peaks at 18.1, 23.2, 24.9, 26.7 and/or 35.1°. The X-ray powder diffraction spectrum of this crystalline form is further characterised by d-spacings of 7.6, 3.8, 3.6, 3.3, 2.5 and 2.4 Å. This crystalline form is further characterised by a DSC curve which shows an endotherm at about 108° C. (peak) with an extrapolated onset at about 89° C., and an exotherm at about 248° C. (peak) with an extrapolated onset at about 241° C. This crystalline form is further characterised by a TGA curve which shows a weight loss of 11.18% between 50 and 125° C., consistent with loss of one mole equivalent of water, followed by further weight loss (decomposition) at about 250° C. This crystalline form is further characterised by solid state $^{13}$C NMR chemical shifts of 16.4, 40.2, 102.8, 159.4 and 172.7 ppm with reference to a value of 176.03 ppm for the carbonyl peak of glycine.

The above-described gaboxadol monohydrate of form I is obtained when gaboxadol hydrochloride (or other addition salt) is neutralised in aqueous solution and the resulting precipitate is collected immediately. By "immediately" it is meant that there is no significant delay between the end of the neutralising process and the collection of the solid, a short period of stirring, subsequent to the addition of neutralising base, is tolerable, e.g. of up to about 1 hour.

However, if the initially-formed precipitate is aged for longer periods, e.g. by stirring the mixture for several hours, preferably overnight or longer, gaboxadol monohydrate in a different crystalline form (herein designated form II) is formed. This crystalline form is characterised by a X-ray powder diffraction spectrum having a peak at 25.2° (2θ). Other peaks that may additionally be present include peaks at 14.0, 19.0, 21.6, 24.8, 26.7 and/or 27.8°. The X-ray powder diffraction spectrum of this crystalline form is further characterised by d-spacings of 7.6, 6.3, 5.7, 4.7, 4.1 and 3.5 Å. This crystalline form is further characterised by a DSC curve which shows an endotherm at about 114° C. (peak) with an extrapolated onset at about 107° C., and an exotherm at about 255° C. (peak) with an extrapolated onset at about 247° C. This crystalline form is further characterised by the TGA curve which shows a weight loss of 10.13% between 75 and 125° C., consistent with loss of one mole equivalent of water, followed by further weight loss (decomposition) at about 250° C. This crystalline form is further characterised by solid state $^{13}$C NMR chemical shifts of 17.5, 40.3, 102.2, 158.5 and 172.5 ppm with reference to a value of 176.03 ppm for the carbonyl peak of glycine.

The above-described conversion of gaboxadol monohydrate of form I into gaboxadol monohydrate of form II is accelerated by addition to the stirred mixture of an alcohol (preferably isopropanol) and/or seed crystals of authentic gaboxadol monohydrate of form II. Therefore an alternative method of preparing crystalline gaboxadol monohydrate of form II comprises the steps of:
  (a) dissolving an acid addition salt of gaboxadol in water;
  (b) adding sufficient base to provide a pH of about 6.5;
  (c) adding isopropanol to the mixture; and
  (d) collecting the product.

All of the above operations are typically carried out at ambient temperature. A preferred base is aqueous sodium hydroxide. In step (b), seed crystals of authentic gaboxadol monohydrate of form II are preferably added after about 0.3 to 0.4 equivalents of base have been added. In step (c), preferably at least an equal volume of isopropanol is added slowly. After addition of isopropanol, the mixture is preferably aged at least one hour. The slurry obtained after step (c) may be wet-milled, if desired, to adjust the particle size distribution. In step (d) the product is typically collected by filtration and may be washed (e.g. with aqueous isopropanol) and dried by conventional means.

The two crystalline polymorphs of gaboxadol monohydrate described above, when heated above 100° C. (e.g. at 110° C.), convert to distinct crystalline polymorphs of gaboxadol anhydrate, designated herein as form I and form II respectively. Gaboxadol anhydrate of form I has a characteristic peak in its X-ray powder diffraction spectrum at 12.8°. Other peaks that may additionally be present include peaks at 16.1, 24.7 and/or 28.5°.

Gaboxadol anhydrate of form II has characteristic peaks in its X-ray powder diffraction spectrum at 16.0, 24.7 and 28.4°, but lacks a peak at 12.8°. The X-ray powder diffraction spectrum of this crystalline form is further characterised by d-spacings of 6.3, 6.1, 5.5, 3.7, 3.6 and 3.1 Å.

Crystalline gaboxadol anhydrate of form I may be converted to crystalline gaboxadol anhydrate of form II by stirring as a suspension in ethanol or other lower alcohol for a period of hours at ambient temperature, preferably 10 hours or longer. "Lower alcohols" refers to alcohols containing up to 6 (preferably up to 4) carbon atoms. Other suitable lower alcohols include methanol and n-propanol, and the conversion may be accelerated by warming. Crystalline gaboxadol anhydrate of form II may also be obtained by stirring a suspension of gaboxadol monohydrate of form I or form II in a lower alcohol, preferably for at least 12 hours and preferably with warming.

Both of the crystalline forms of gaboxadol monohydrate and both of the crystalline forms of gaboxadol anhydrate are suitable for incorporation in pharmaceutical formulations. In particular, these novel polymorphs of gaboxadol free base may be incorporated in conventional oral dosage formulations such as tablets using conventional techniques and equipment without the risk of corrosion. Furthermore, in view of their significant degree of solubility in water, the novel polymorphs are expected to show bioavailability equivalent to that of the acid addition salts previously used for this purpose.

Gaboxadol monohydrate of form II is thermodynamically more stable than the monohydrate of form I, and is therefore the preferred monohydrate for pharmaceutical use. Similarly, gaboxadol anhydrate of form II is more stable than the anhydrate of form I, and is the preferred anhydrate for pharmaceutical use. (The anhydrate of form I reverts to the monohydrate at 25° C./70% RH, while the anhydrate of form I reverts to the monohydrate at 25° C./90% RH). The monohydrate form II has a safer thermal profile than the anhydrous form II based on thermal decomposition studies.

According to a further aspect of the invention there is provided a pharmaceutical composition comprising, in a pharmaceutically acceptable carrier, gaboxadol monohydrate of form I or form II as defined above, or gaboxadol anhydrate of form I or form II as defined above, or any combination thereof. Preferably, said composition contains gaboxadol monohydrate of form II or gaboxadol anhydrate of form II. Most preferably, said composition contains gaboxadol monohydrate of form II.

The pharmaceutical composition of this invention is a pharmaceutical preparation, for example, in solid, semisolid or liquid form, which contains one or more of the compounds of the present invention as an active ingredient in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea and other carriers suitable for use in manufacturing preparations in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Compositions for inhalation or insufflation include suspensions in pharmaceutically acceptable aqueous or organic solvents, or mixtures thereof, and powders. The liquid or solid compositions may contain suitable pharmaceutically acceptable excipients as set out above. Such compositions are administered by the oral or nasal respiratory route for local or systemic effect. Suspension or powder compositions may be administered, preferably orally or nasally, from devices which deliver the formulation in an appropriate manner.

The pharmaceutical composition of the invention is preferably in a form suitable for oral administration, such as tablets or capsules.

Methods and materials for the formulation of active ingredients as pharmaceutical compositions are well known to those skilled in the art, e.g. from texts such as Remington's Pharmaceutical Sciences (Mack Publishing, 1990).

Crystalline gaboxadol monohydrate or anhydrate in accordance with the invention is useful in therapeutic treatment of the human body, and in particular the treatment of disorders susceptible to amelioration by $GABA_A$ receptor agonism.

Accordingly, the invention further provides a method of treating disorders susceptible to amelioration by $GABA_A$ receptor agonism comprising administering to a patient in need thereof a therapeutically effective amount of crystalline gaboxadol monohydrate of form I or form II as defined above, or of crystalline gaboxadol anhydrate of form I or form II as defined above.

The invention further provides the use of crystalline gaboxadol monohydrate of form I or form II as defined above, or of crystalline gaboxadol anhydrate of form I or form II as defined above, for the manufacture of a medicament for treatment of disorders susceptible to amelioration by $GABA_A$ receptor agonism.

In a particular embodiment of the invention, the disorder is susceptible to amelioration by agonism of $GABA_A$ receptors comprising α4 and δ subunits.

In a further embodiment of the invention, the disorder is selected from neurological or psychiatric disorders such as epilepsy, Parkinson's disease, schizophrenia and Huntington's disease; sleep disorders such as insomnia; premenstrual syndrome; hearing disorders such as tinnitus; vestibular disorders such as Meniere's disease; attention deficit/hyperactivity disorder; intention tremor; and restless leg syndrome.

In a still further embodiment of the invention, the disorder is a sleep disorder, in particular insomnia such as primary insomnia, chronic insomnia or transient insomnia. Within this embodiment is provided the use of the compounds of this invention for the manufacture of a medicament for increasing total sleep time, increasing non-REM (rapid eye movement) sleep time and/or decreasing sleep latency.

The compounds of this invention may be administered to patients in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician.

A typical dose is in the range from about 5 mg to about 50 mg per adult person per day, e.g. 5 mg, 10 mg, 15 mg, 20 mg or 25 mg daily.

EXAMPLES

Example 1

Preparation of Gaboxadol Monohydrate of Form I.

A solution of gaboxadol hydrochloride (approximately 10% w/w) was treated with sufficient triethylamine to give a pH of 6.5. The resulting white solid was collected by filtration and air dried.

The X-ray powder diffraction spectrum was recorded at ambient temperature (CuKα radiation, 3° to 40° (2θ), steps of 0.014°, 0.2 sec per step), giving the results summarised below.

A DSC trace was recorded between 25 and 300° C. (10° C./min), under a flow of dry nitrogen, giving the results summarised below.

TGA was carried out between 25 and 300° C. (10° C./min), under a flow of dry nitrogen, giving the results summarised below.

Summary of Data for gaboxadol monohydrate of Form I.

XRPD

Main peak at 11.5°, subsidiary peaks at 18.1, 23.2, 24.9, 26.7 and 35.1°; d-spacings of 7.6, 6.3, 5.7, 4.7, 4.1 and 3.5 Å.

DSC
 Endotherm at 114° C. (peak, extrapolated onset 107° C.), exotherm 255° C. (peak, extrapolated onset 247° C.).

TGA
 Weight loss of 10.13% between 75 and 125° C. and further weight loss (decomposition) above 250° C.

Solid State $^{13}$C NMR
 16.4, 40.2, 102.8, 159.4 and 172.7 ppm with reference to a value of 176.03 ppm for the carbonyl peak of glycine.

Example 2

Preparation of Gaboxadol Monohydrate of Form II.

The procedure of Example 1 was repeated, but before collecting the solid by filtration, the mixture was stirred approximately 60 hours at ambient temperature.

The X-ray powder diffraction spectrum was recorded at ambient temperature (CuKα radiation, 3° to 40° (2θ), steps of 0.014°, 0.3 sec per step), giving the results summarised below.

A DSC trace was recorded between 25 and 300° C. (10° C./min), under a flow of dry nitrogen, giving the results summarised below.

TGA was carried out between 25 and 300° C. (10° C./min), under a flow of dry nitrogen, giving the results summarised below.

Summary of Data for gaboxadol monohydrate of Form II.

XRPD
 Main peak at 25.2°, subsidiary peaks at 14.0, 19.0, 21.6, 24.8, 26.7 and 27.8°; d-spacings of 7.6, 3.8, 3.6, 3.3, 2.5 and 2.4 Å.

DSC
 Endotherm at 108° C. (peak, extrapolated onset 89° C.), exotherm 248° C. (peak, extrapolated onset 241° C.).

TGA
 Weight loss of 11.18% between 50 and 125° C. and further weight loss (decomposition) above 250° C.

Solid State $^{13}$C NMR
 17.5, 40.3, 102.2, 158.5 and 172.5 ppm with reference to a value of 176.03 ppm for the carbonyl peak of glycine.

Example 3

Preparation of Gaboxadol Monohydrate of Form II

Gaboxadol hydrochloride (300 g, 1.698 mol) and water (1.2 L) were charged into a 5.0 L resin kettle equipped with temperature control bath, overhead stirrer, N$_2$ inlet, and flow-cell wet mill apparatus at ambient temperature (25° C.). 5N NaOH (102 mL, 0.3 equiv, 0.509 mol) was charged over five minutes at ambient temperature and the solution was aged for 30 min. The batch was seeded with Gaboxadol monohydrate form II (15.0 g, 5 wt %). 5 N NaOH (238 mL, 1.189 mol) was added over 3 h via a syringe pump while the internal temperature of the vessel was maintained at 25° C. The pH of the reaction slurry is carefully monitored during the base charge with a calibrated pH electrode. When the pH had risen to ~5.5 the syringe motor was turned off and the remaining base (~2 mL) was manually discharged from the syringe dropwise until a pH of 6.5 was obtained. The slurry was further aged for 1 h at ambient temperature. iPrOH (1.86 L) was added dropwise over 2 h at ambient temperature. The slurry was aged with stirring for 1 h. The batch was cooled to an internal temp to 0-10° C. and wet milled at 0-10° C. The slurry was allowed to warm up to ambient temperature (20° C.) and filtered. The wet cake was displacement washed 3×600 mL of 30% water/iPrOH and vacuum/suction dried at 1 atm or reduced pressure under humidity controlled N$_2$ (>15% RH) to give gaboxadol monohydrate form II.

Example 4

Preparation of Gaboxadol Monohydrate of Form II

Gaboxadol hydrobromide (100 g, 0.452 mol) and water (300 mL) were charged into a 2 L vessel equipped with an overhead stirrer, N$_2$ inlet, and additional funnel at ambient temperature (25° C.). 5N NaOH (31 mL, 0.4 equiv, 0.158 mol) was charged over five minutes at ambient temperature and the solution was aged for 30 min. The batch was seeded with Gaboxadol monohydrate form II (15.0 g, 5 wt %). 5 N NaOH (54 mL) was added over 3 h via a syringe pump while the internal temperature of the vessel was maintained at 25° C. The pH of the reaction slurry is carefully monitored during the base charge with a calibrated pH electrode. The slurry was further aged for 1 h at ambient temperature. iPrOH (450 mL) was added dropwise over 2 h at ambient temperature. The slurry was aged with stirring for 1 h. After wet mill, the slurry was allowed to warm up to ambient temperature (20° C.) and filtered. The wet cake was displacement washed 3×150 mL of 30% water/iPrOH and vacuum/suction dried at 1 atm or reduced pressure under humidity controlled N$_2$ (>15% RH) to give gaboxadol monohydrate form II.

Example 5

Preparation of Gaboxadol Anhydrate of Form I

A sample of the product from Example 1 was heated at 110° C. at atmospheric pressure for 1.25 hours. The X-ray powder diffraction spectrum of the resulting solid was recorded at ambient temperature (CuKα radiation, 3° to 40° (2θ), steps of 0.014°, 0.1 sec per step), giving a peak at 12.8° and further peaks at 16.1, 24.7 and 28.5°.

Example 6

Preparation of Gaboxadol Anhydrate of Form II

A sample of the product from Example 2 was heated at 110° C. at atmospheric pressure for 1.25 hours. The X-ray powder diffraction spectrum of the resulting solid was recorded at ambient temperature (CuKα radiation, 3° to 40° (2θ), steps of 0.014°, 0.3 sec per step), giving peaks at 16.0, 24.7 and 28.4°; and d-spacings of 6.3, 6.1, 5.5, 3.7, 3.6 and 3.1 Å.

Example 7

Conversion of Gaboxadol Anhydrate of Form I to Gaboxadol Anhydrate of Form II

A sample of the product of Example 5 was suspended in ethanol and stirred at ambient temperature overnight. The resulting solid was collected by filtration and air dried. Its X-ray powder diffraction spectrum matched that of the product of Example 6.

All x-ray powder diffraction spectra were obtained using a Bruker D8 Advance diffractometer equipped with a PSD detector in the Bragg-Bretano (θ-θ) geometry, run at 40 kV and 40 mA.

The invention claimed is:

1. The compound gaboxadol monohydrate in a crystalline form selected from:
   (a) form I which is characterised by an X-ray powder diffraction spectrum in 2θ values using CuKα radiation having a peak at 11.5°; and
   (b) form II which is characterised by an X-ray powder diffraction spectrum in 2θ values using CuKα radiation having a peak at 25.2°.

2. The compound of claim 1 which is crystalline gaboxadol monohydrate of form II which is characterised by an X-ray powder diffraction spectrum in 2θ values using CuKα radiation having a peak at 25.2°.

3. The compound of claim 2 which is additionally characterised by solid state $^{13}$C NMR chemical shifts of 17.5, 40.3, 102.2, 158.5 and 172.5 ppm with reference to a value of 176.03 ppm for the carbonyl peak of glycine.

4. The compound gaboxadol anhydrate in a crystalline form selected from:
   (a) form I which is characterised by an X-ray powder diffraction spectrum in 2θ values using CuKα radiation having a peak at 12.8°; and
   (b) form II which is characterised by an X-ray powder diffraction spectrum in 2θ values using CuKα radiation having a peak at one or more of 16.0°, 24.7° and 28.4°.

5. The compound of claim 4 which is crystalline gaboxadol anhydrate of form II which is characterised by an X-ray powder diffraction spectrum in 2θ values using CuKα radiation having a peak at one or more of 16.0°, 24.7° and 28.4° in the absence of a peak at 12.8°.

* * * * *